United States Patent [19]

Louthan

[11] Patent Number: 4,670,602
[45] Date of Patent: Jun. 2, 1987

[54] METHOD OF MAKING DISULFIDES USING A COMBINATION REACTION VESSEL AND ASPIRATOR-MIXER

[75] Inventor: Rector P. Louthan, Bartlesville, Okla.
[73] Assignee: Phillips Petroleum Co., Bartlesville, Okla.
[21] Appl. No.: 643,349
[22] Filed: Aug. 23, 1984

Related U.S. Application Data

[62] Division of Ser. No. 177,315, Aug. 12, 1980, Pat. No. 4,483,826.

[51] Int. Cl.$^4$ ............................................. C07C 149/12
[52] U.S. Cl. ......................................... 568/26; 568/25
[58] Field of Search .................................. 568/25, 26

[56] References Cited

U.S. PATENT DOCUMENTS

| | | | |
|---|---|---|---|
| 1,968,842 | 8/1934 | Malisoff | 568/26 |
| 2,127,571 | 8/1938 | Pardee | 23/154 |
| 2,517,934 | 8/1950 | Schulze | 568/26 |
| 2,535,833 | 12/1950 | Bond | 568/26 |
| 2,695,263 | 11/1954 | Krause | 196/29 |
| 2,727,852 | 12/1955 | Brown | 196/33 |
| 3,117,077 | 1/1964 | Brooke | 208/195 |
| 3,329,708 | 7/1967 | Berger | 260/500 |
| 3,340,324 | 9/1967 | Warner | 568/26 |
| 3,547,811 | 12/1970 | McWhirter | 210/7 |
| 4,207,180 | 6/1980 | Chang | 210/7 |

OTHER PUBLICATIONS

N. Kharasch (ed.), Organic Sulfur Compounds, p. 97 (1961) Pergamon Press, N.Y. QD 412.51.

Primary Examiner—Donald G. Daus
Assistant Examiner—Mary E. Ceperley
Attorney, Agent, or Firm—A. W. Umphlett

[57] ABSTRACT

There are disclosed a method and apparatus for effecting a chemical reaction. There is provided an aspirator-mixer or zone to which the reaction mass is pumped to activate the same and into which another reactant is furnished and from which admixed reaction mass and reactant are discharged into a reaction zone in which the concentration or proportion of a vaporous or gaseous reactant is maintained at a level as desired by sucking therefrom into the suction side of the aspirator-mixer or zone any excess of such reactant. In one embodiment, a mercaptan is oxidized to corresponding disulfides with oxygen and the oxygen level in the reaction zone is maintained as desired by sucking off into the suction side of the aspirator-mixer any oxygen in the reaction zone in excess of that desired therein.

8 Claims, 2 Drawing Figures

METHOD OF MAKING DISULFIDES USING A COMBINATION REACTION VESSEL AND ASPIRATOR-MIXER

This application is a divisional application of application Ser. No. 177,315, now U.S. Pat. No. 4,483,826.

BRIEF DESCRIPTION OF INVENTION

A reactant, e.g., a mercaptan, is reacted with an oxidizing medium, e.g., oxyen, by admixture of the reactant and oxidizing medium in an aspirator-mixer, the admixture thus obtained is passed into a reaction vessel, the reaction mass from said vessel is used to activate the aspirator-mixer and means are provided for returning from the vapor state in said vessel a desired amount of unreacted oxidizing medium to said aspirator whereby the amount of oxidizing medium present in said vessel at any time is controlled. In one embodiment of the invention, n-butyl mercaptan is converted to di-n-butyl disulfide.

DETAILED DESCRIPTION

Figure 1:
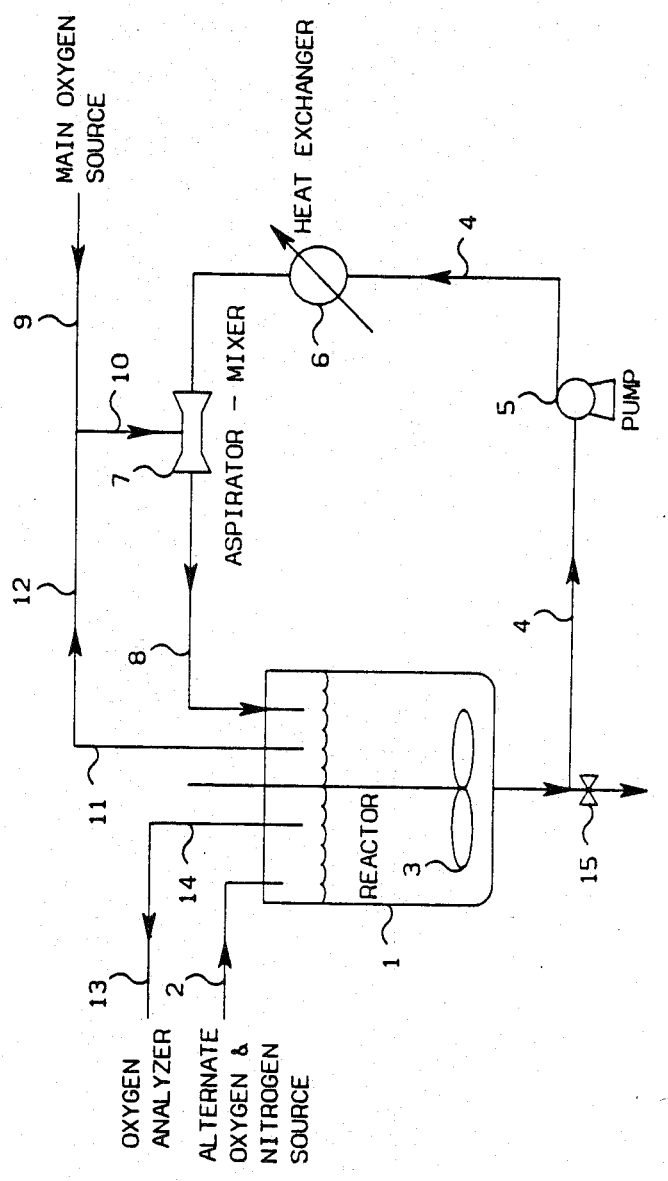
FIG. 1 is a diagrammatic showing of the principal steps of the invention as embodied in one form of an apparatus according to the invention.

This invention relates to effecting a chemical reaction. In one of its aspects, the invention relates to the oxidation of a reaction material, e.g., a thiol or mercaptan to produce a corresponding disulfide therefrom. In another of its aspects, the invention relates to the oxidation of a thiol or mercaptan in a controlled manner. In one of its more specific aspects, it relates to a method and apparatus to carry out a reaction in which at least one reactant present in the reaction zone is controlled. In one of its concepts, the invention provides a process for the conversion of a liquid reactant with the aid of an oxidizing medium which are admixed in a zone of intense admixing maintained under reduced pressure, e.g., in an aspirator-mixer, the admixture obtained is passed to a reaction vessel for further reaction thereof, oxidizing medium undesired in said reaction vessel is removed therefrom to said zone of intense admxing under reduced pressure, and reaction mass is removed from said vessel and used to activate said zone of intense admixing under reduced pressure. In another of its concepts, the invention involves, say, the conversion of a thiol or mercaptan to the corresponding disulfide by the reaction with an oxidizing medium, e.g., oxygen, by bringing the reactants together in an aspirator-mixer, discharging said mixture thus obtained in the reaction vessel for further reaction, removing reaction mass from said vessel and using the same to activate said aspirator-mixer, and removing the medium from the vapor state in said reaction vessel into said aspirator-mixer thus to control the amount of oxidizing medium in said vessel at any given time.

More specifically, in one of its concepts, the invention provides an oxidation process wherein a mercaptan is intimately admixed with an alcoholic alkali metal hydroxide solution and then with gaseous oxygen in a aspirator-type mixing device for conversion to a corresponding disulfide, the invention being characterized in that excess unreacted oxygen is removed by a suction action from the reaction mass or vessel and readmitted to the aspirator-type mixing device for further use in subsequent reactions, in such a closed system.

U.S. Pat. No. 2,517,934, issued Aug. 8, 1950, discloses a process for conversion of a mercaptan dissolved in an alkyl disulfide in a catalytic oxidation zone with dissolved oxygen-containing gas to convert the mercaptan to the corresponding disulfide. A mixing chamber 12 for admixing air with the mercaptan-containing solution is shown and described. U.S. Pat. No. 2,695,263, issued Nov. 22, 1954, discloses a cupric chloride sweetening of a sour type naphtha. Oxygen is introduced by 22 into admixture with sour cracked oil or naphtha in 17 and the admixture thus obtained is passed through mixer 18 for thorough intermingling.

U.S. Pat. No. 3,117,077, issued Jan. 8, 1954, also discloses a sweetening of mercaptan containing hydrocarbons and shows the injection of air or free oxygen containing gas at 18 for admixture with the sour hydrocarbon. The admixture then is passed to contacting zone 17 into which feed reagents described in the patent are introduced.

U.S. Pat. No. 3,340,324, issued Sept. 5, 1967, describes a method for producing disulfides from mercaptans and shows in graphic form rates of certain reactions therein described.

The disclosures of the above mentioned patents are incorporated herein by this reference to them.

The execution of the concept or concepts of the present invention greatly increase the rate of conversion of mercaptans to disulfides. The amount of excess unreacted oxygen is maintained, according to the invention, at any desired level, by recycling the oxygen into the aspirator-mixer.

It is an object of this invention to effect a chemical reaction. It is another object of this invention to convert a mercaptan into a disulfide. It is a further object of the invention to provide a method for converting a thiol or mercaptan into a corresponding disulphide using oxygen or an oxygen-containing gas. It is still a further object of the invention to provide an apparatus for the conversion of a reactant under controlled conditions, e.g., a conversion of a mercaptan to a disulfide wherein the amount of excess unreacted oxygen is maintained at a desired level of value.

Other aspects, concepts, objects and the several advantages of the invention are apparent from a study of this disclosure, the drawing, and the appended claims.

According to the present invention, there is provided a process for the conversion of a reactant with the aid of an oxidizing medium which comprises bringing together said reactant and said medium in a zone of intense admixing under reduced pressure, passing the mixture thus obtained in the reaction zone to complete as far as possible the conversion reaction thus intended, providing a vapor communication between said reaction zone and said mixing zone and removing from said reaction zone into said mixing zone said vapor communicating any oxidizing medium in excess of that desired to maintain in said reaction zone.

In view of its particular applicability to the oxidation of mercaptans to the corresponding disulfides, the invention is now described in connection with such conversion.

INVENTION BACKGROUND

Thiols useful in this invention are those materials represented by the formula, RSH, wherein R can be any alkyl, cycloalkyl, or aryl radical having one to twenty carbon atoms. Exemplary of these type compounds are:
 methanethiol
 ethanethiol
 1-propanethiol
 2-propanethiol
 1-butanethiol (n-butyl mercaptan)
 2-butanethiol
 1-thiol-2-methylpropane
 2-methyl-2-propanethiol
 1-hexanethiol
 1-dodecanethiol
 1-pentadecanethiol
 1-eicosanethiol
 cyclohexanethiol
 benzenethiol
and the like.

Catalysts useful in this invention are any soluble or otherwise homogeneous materials known to be active in converting mercaptans to disulfides. One such type catalyst can be any alkali metal or alkali earth metal salt of an alcohol dissolved in preferably the same alcohol. For example, the most preferred is sodium hydroxide dissolved in methyl, ethyl, propyl or butyl alcohol. Other such type catalysts are amines dissolved in a solvent.

Solvents are not particularly required in this invention so long as the media is liquid in order to enable pumping. Solvents can, when used, be alcohols, hydrocarbons, or any liquid inert in the system.

Temperature is not critical in this invention since it depends upon the particular mercaptan being employed and the size and type of reactor employed. The oxygen pressure is such so as to avoid explosive mixtures. Air or pure oxygen can be employed in this invention. It is, however, preferred to employ pure oxygen because no build-up of unwanted excess nitrogen is obtained which would otherwise necessitate venting during operations.

Referring now to FIG. 1 of the drawing, there is shown an operation according to the invention in which conversion of mercaptan to disulfide is accomplished by charging mercaptan, alcohol and alkali metal hydroxides to reactor 1. The reactor is closed and pressured with nitrogen introduced at 2. The stirrer 3 is started. Pump 5 withdraws vessel contents through 4, pumps these through heat exchanger 6 into aspirator 7. Aspirator 7 effects oxygen introduced at 9 through 10 into admixture with the liquid being pumped into and through aspirator-mixer 7, contents of which are discharged by 8 into vessel 1. As shown, oxygen not desired to be maintained in vessel 1 is removed in this embodiment by way of line 11 and 12, to 10 and into aspirator-mixer 7. Oxygen which is needed in aspirator-mixer 7 enters the reaction almost immediately upon the admixing which takes plate in the aspirator-mixer 7. The sucking action of the aspirator-mixer 7 will remove from vessel 1 vapor feasibly employed, is a control valve of system which will adjust the amount of vapor and/or gas removed from vessel 1 into aspirator-mixer 7.

One skilled in the art in possession of this disclosure having studied the same will recognize that with the use of this invention there is eliminated any desired or dangerous proportions of oxygen in the overall system. In the embodiment now described, the oxygen was held at about 15–20 mole percent and monitored by an oxygen analyzer 13 to which material from the vapor state in vessel 1 was fed by 14.

The rate of mercaptan conversion is determined by periodically removing samples by 15. These were analyzed by gas-liquid state chromatography (GLC).

When the reaction is complete, the flow of oxygen is arrested and the liquid is continued to be circulated until improved ambiance or room temperature. The reactor is then vented and liquid drained through valve 15 for further treatment.

The following examples are given to more fully describe and illustrate the invention.

EXAMPLE I

Figure 2:
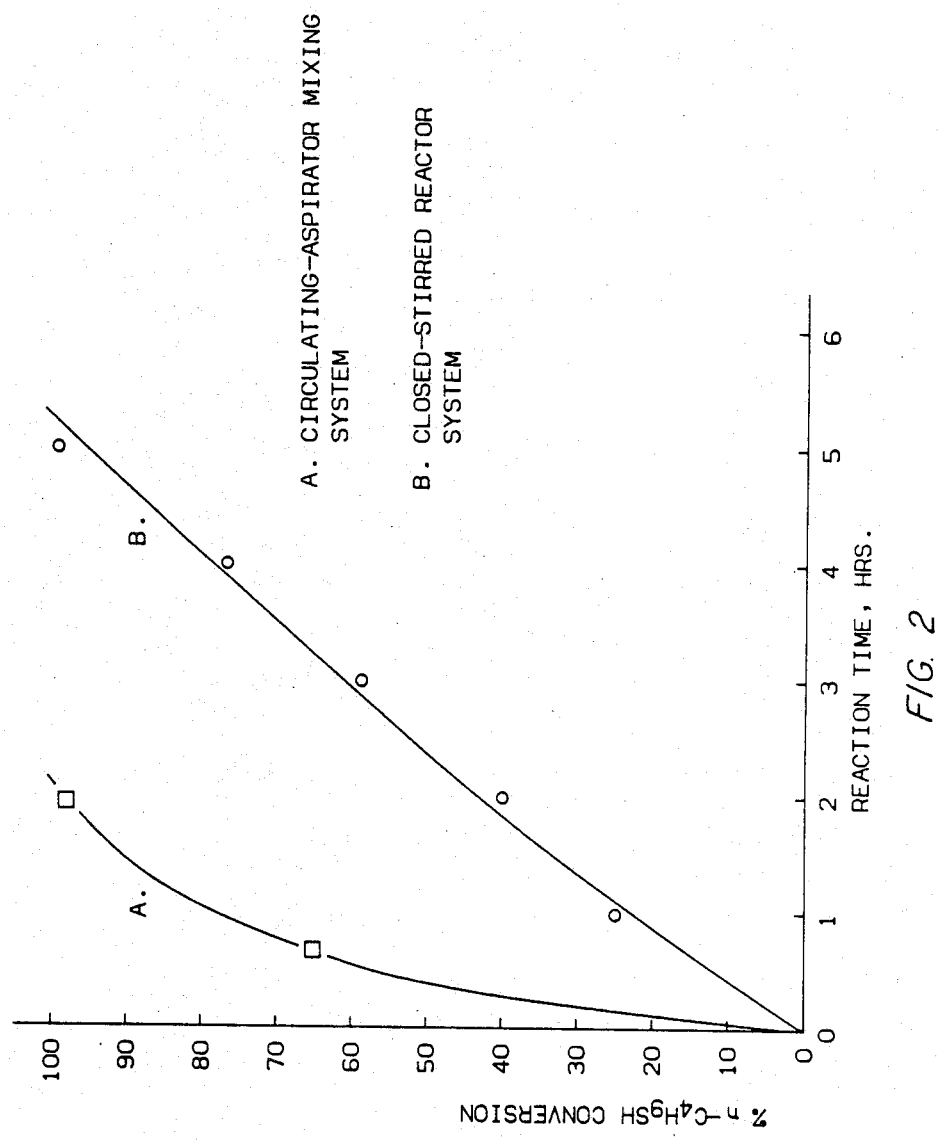
FIG. 2 shows the effect of the reaction system of the invention on the rate of conversion of a mercaptan, e.g., n-butyl mercaptan to form di-n-butyldisulfide.

This example is a control and illustrates the yield and rate of formation of di-n-butyl disulfide from n-butyl mercaptan when the reaction is conducted in a single reactor closed system. Into a 10-gallon glasslined, jacketed reactor equipped with a thermocouple, stirrer and cooling coils was charged 38 pounds (0.42 pound moles) of n-butyl mercaptan, 17.2 pounds (0.537 pound moles) of methanol and 0.91 pounds (0.023 pound moles) of sodium hydroxide. The reactor was sealed and pressured with nitrogen to 220 psig. The stirrer was started and oxygen was added to the vapor phase such that the total reactor pressure was 250 psig. The system was connected to a Scott oxygen analyzer, model 0T0X90, and the amount of oxygen present was maintained at 20 mole percent. Throughout the run the amount of oxygen present was maintained at about 15 to 20 mole percent. Within 10 minutes after the oxygen was added, the temperature began to slowly rise from about 23° C. (73° F.) to about 62° C. (144° F.) where it was maintained by circulating cold oil through the jacket. During the run, samples were periodically withdrawn and analyzed by GLC using a 60.9 cm (2 ft.)×0.64 cm (0.25 in.) silicone rubber column programmed between 50° C. to 300° C. at 25° C. per minute rise using a helium flow of 60 milliliters per minute. The analyses which are shown in Table I and FIG. 2 indicate the reaction required five hours to complete. The reactor was cooled to ambient room temperature, vented and the contents discharged. The bottom oil phase, 33.2 pounds, was washed with an equal volume of water, and dried by passing air at 6 cfh through the oil and 100°–120° C. for 24 hours. In this way there was obtained 31.95 pounds (85 mole percent yield) of essentially pure di-n-butyl disulfide.

EXAMPLE II

This example illustrates the invention and shows that when the reaction liquid is circulated through a restricted area (aspirator) such that a more intimate contact with oxygen is made, the rate of reaction (rate of mercaptan conversion) is greatly increased. A 10-gallon glass-lined reactor, equipped with a Scott oxygen analyzer, reflux condenser, stirrer, thermocouple and circulating inlet tube as shown in FIG. 1 was charged with 38 pounds (0.42 pound moles) of n-butyl mercaptan, 17.2 pounds (0.432 pound moles) of methyl alcohol and 0.91 pounds (0.023 pound moles) of sodium hydroxide. The reactor was sealed and pressured with nitrogen to 220 psig. The stirrer was started and the liquid externally circulated at 1.5–2 gallons per minute using a Lawrence can pump by first passage through a heat exchanger and then being passed through an Ametex water jet exhauster (aspirator) having a 1.27 cm (0.50 in.) opening on the circulated side and a 0.635 cm (0.25 in.) opening on the suction side. The liquid was then returned to the vapor phase of the reactor. Oxygen was then added such that entry was made through the aspirator (see FIG. 1). The system was pressured to about 280 psig with the additional oxygen and the amount of oxygen present in the vapor phase of the reactor monitored by a Scott analyzer and maintained at about 20 mole percent. The reaction temperature immediately began to slowly rise such that after about 1 hour the temperature in the liquid phase of the reactor was about 60° C. (140° F.). The temperature was maintained between about 49° C.–60° C. (120° F.–140° F.) throughout the run. After 1 hour analysis indicated the reaction was 65 percent complete and after 2 hours the reaction was complete as determined by GLC. The product was separated and dried as previously described to give 33.3 pounds (88.6 mole percent yield) of essentially pure di-n-butyl disulfide. A comparison of the rates of reaction carried out by the closed system (Example I) and the circulating-intimate mixing system (Example II) is shown in Table I and FIG. II. When another run employing the method described in Example II was carried out wherein the separated oil was distilled rather than air dried at 100° C.–120° C., the yield of di-n-butyl disulfide was increased giving 35 pounds (93.1 mole percent) of product.

TABLE I

Summary - Synthesis of Di-n-butyl Disulfide

| Charge: | 38 pounds of n-Butyl Mercaptan |
| | 17.2 pounds Methyl Alcohol |
| | 0.91 pounds Sodium Hydroxide |
| Temp.: | 49–60° C.; Press: 220 psig $N_2$ + 30–60 psig $O_2$ (20 mole percent) |

| | Wt. % n-Butyl Mercaptan Conversion by GLC | |
|---|---|---|
| Reaction Time, Hrs. | Example I-Stirred Autoclave | Example II-Aspirator-Loop Reactor |
| 1 | 25 | 65 |
| 2 | 40 | 98 |
| 3 | 59 | — |
| 4 | 77 | — |
| 5 | 98 | — |
| Mole % Yield of Separated Di-n-Butyl Disulfide | 85 | 88.6 |

Reasonable variation and modification are possible within the scope of the foregoing disclosure, drawings and the appended claims to the invention, the essence of which is that by use of an aspirator-mixer, zone or device, reactants to the admixture are immediately admixed, the reaction initiated, and completed in a reaction zone or vessel from which gasesous vapors undesired therein are removed to the suction side of said aspirator-mixer; in one embodiment, now preferred, a mercaptaan is converted to disulfide by oxidation according to known chemical reactions effected in the method and/or apparatus of the invention.

I claim:

1. A process for the conversion of a mercaptan reactant to disulfide product with the aid of gaseous oxygen medium which comprises continuously bringing together a reaction mixture consisting essentially of said mercaptan reactant, an alcoholic alkali metal hydroxide solution and said gaseous oxygen medium in a zone of intense admixing under reduced pressuring using an aspirator-mixer, passing the admixture thus obtained into a reaction zone to complete as far as possible the conversion reaction of mercaptan to disulfide thus intended, continuously passing at least a portion of said admixture from said reaction zone through said aspirator-mixer, providing vapor communication between said reaction zone and said mixing zone and removing from said reaction zone to said mixing zone with said vapor communication any gaseous oxygen medium in excess of that desired to be maintained in said reaction zone.

2. A process according to claim 1 wherein the mercaptan reactant is a liquid.

3. A process according to claim 2 wherein said mercaptan is n-butyl mercaptan and the disulfide product is di-n-butyl disulphide.

4. A process according to claim 2 wherein the mercaptan is one represented by the formula RSH wherein R is selected from alkyl, cycloalkyl and aryl radicals having 1–20 carbon atoms.

5. A process according to claim 2 wherein the mercaptan is n-butyl mercaptan in admixture with an alcohol and the alkali metal hydroxide is sodium hydroxide.

6. In a process for the oxidation of liquid oxidizable mercaptans to disulfides in an alcoholic alkali metal hydroxide solution in the presence of oxygen in a reaction zone, the improvement of reducing the hazardous build up of unreacted or excessive oxygen which comprises, cycling at least a portion of the reaction mixtures removed from said reaction zone through an aspirator-mixing zone and back into the vapor phase of said reaction zone, withdrawing vapors or gaseous undesired reactants and oxygen from the vapor phase of said reaction zone, and introducing said undesired gaseous reactants and oxygen into said aspirator-mixing zone for intimate contacting, mixing and further reacting with said reaction mixture passed therethrough.

7. A process according to claim 6 for the conversion of n-butyl mercaptan to di-n-butyl disulfide.

8. A process according to claim 7 wherein said n-butyl mercaptan which is converted to di-n-butyl disulfide is in admixture with methanol and sodium hydroxide.

* * * * *